United States Patent
Tsai et al.

(10) Patent No.: US 11,291,654 B2
(45) Date of Patent: Apr. 5, 2022

(54) FORMULATIONS OF CYCLOSERINE COMPOUNDS AND APPLICATIONS THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Hsin-Hsin Yang, New Taipei (TW); Hsuan-Ang Tsai, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 61 days.

(21) Appl. No.: 16/130,747

(22) Filed: Sep. 13, 2018

(65) Prior Publication Data

US 2020/0085792 A1 Mar. 19, 2020

(51) Int. Cl.
| | |
|---|---|
| *A61K 31/42* | (2006.01) |
| *A61K 9/48* | (2006.01) |
| *A61K 9/20* | (2006.01) |
| *A61K 9/28* | (2006.01) |
| *A23L 33/10* | (2016.01) |
| *A61P 25/28* | (2006.01) |
| *A61P 25/24* | (2006.01) |
| *A61P 25/22* | (2006.01) |
| *A61P 25/18* | (2006.01) |
| *A61P 25/16* | (2006.01) |
| *A61P 31/06* | (2006.01) |

(52) U.S. Cl.
CPC .............. *A61K 31/42* (2013.01); *A23L 33/10* (2016.08); *A61K 9/2009* (2013.01); *A61K 9/2018* (2013.01); *A61K 9/2054* (2013.01); *A61K 9/2059* (2013.01); *A61K 9/2063* (2013.01); *A61K 9/2086* (2013.01); *A61K 9/282* (2013.01); *A61K 9/2846* (2013.01); *A61K 9/2866* (2013.01); *A61K 9/2886* (2013.01); *A61K 9/485* (2013.01); *A61K 9/4858* (2013.01); *A61K 9/4866* (2013.01); *A61K 9/4891* (2013.01); *A61P 25/16* (2018.01); *A61P 25/18* (2018.01); *A61P 25/22* (2018.01); *A61P 25/24* (2018.01); *A61P 25/28* (2018.01); *A61P 31/06* (2018.01); *A23V 2002/00* (2013.01); *A23V 2200/322* (2013.01)

(58) Field of Classification Search
CPC ...... A61K 31/42; A61K 33/10; A61K 9/2009; A61K 9/2018; A61K 9/2054; A61K 9/2059; A61K 9/2063; A61K 9/2086; A61K 9/282; A61K 9/2846; A61K 9/2866; A61K 9/2886; A61K 9/485; A61K 9/4858; A61K 9/4866; A61K 9/4891; A61P 25/28; A61P 25/22; A61P 25/18; A61P 25/24; A61P 25/16; A61P 31/06; A23V 2002/00; A23V 2200/322
See application file for complete search history.

(56) References Cited

U.S. PATENT DOCUMENTS

| | | | | |
|---|---|---|---|---|
| 2009/0214645 | A1* | 8/2009 | Kramer | A61K 9/1623 424/474 |
| 2014/0018349 | A1* | 1/2014 | Heresco-Levy | A61K 31/42 514/211.13 |
| 2014/0302132 | A1* | 10/2014 | Brown | A61K 9/145 424/452 |
| 2018/0000810 | A1* | 1/2018 | Gupta | A61K 9/0095 |

FOREIGN PATENT DOCUMENTS

| | | |
|---|---|---|
| WO | 2017/107242 A1 | 6/2017 |
| WO | WO-2018043850 A1 * | 3/2018 ............... A61K 9/00 |
| WO | 2018/043850 A1 | 8/2018 |

OTHER PUBLICATIONS

English machine translation of Kim et al. (WO 2018/043850 A1; published Mar. 8, 2018) made Mar. 18, 2020. (Year: 2020).*
Taiwanese FDA, Western medicine, medical equipment, cosmetics license query, License Details for The Department of Health Pharmaceuticals No. 048573. Retrieved from URL: https://info.fda.gov.tw/MLMS/H0001D.aspx?Type=Lic&LicId=01048573, issued on Feb. 2, 2007.

* cited by examiner

*Primary Examiner* — Michael B. Pallay
(74) *Attorney, Agent, or Firm* — McDermott Will & Emery LLP

(57) ABSTRACT

Formulations comprising cycloserine compounds and one or more enteric materials in a solid dosage form, and uses thereof for treating and/or reducing the risk of a neuropsychiatric disorder or tuberculosis.

24 Claims, No Drawings

FORMULATIONS OF CYCLOSERINE COMPOUNDS AND APPLICATIONS THEREOF

BACKGROUND OF THE INVENTION

D-Cycloserine (i.e., 4-amino-3-isoxazolidinone), is a natural product of *Streptomyces orchidaceus* and *Streptomyces garyphalus*, which acts as a competitive antagonist of D-alanine, one component of bacterial cell walls. D-cycloserine inhibits alanine racemase and alanine synthetase, resulting in bacterial cell walls damaging due to deficiency of D-alanine. D-cycloserine has been known as an antibiotic drug since the late 1950s and marketed in the gelatin capsule form under a brand name Seromycin®. It was classified on the World Health Organization's List of Essential Medicines as a second-line drug for the treatment of multidrug-resistant tuberculosis (MDR-TB). However, D-cycloserine is found to be unstable under acidic and/or aqueous conditions and the gelatin capsule form is unable to improve such instability, resulting in less favorable absorption in the gastrointestinal tract.

In addition to be an antibiotic, D-cycloserine is found to be a partial agonist/antagonist of the glycine/D-serine coagonist site of N-methyl-D-aspartate (NMDA) receptors and is readily available for the central nervous system (CNS) after administration peripherally. As a selective partial NMDA-agonist, it was later proven that D-cycloserine improves long-term potentiation (LTP), a neuronal mechanism thought to be relevant for learning processes. D-cycloserine plays dual function in regulating NMDA receptors—it acts as a positive modulator at low doses but as a negative modulator at high doses. Overdosing with D-cycloserine may result in paresis, seizures, and coma. Other side effects associated with improper dosing of D-cycloserine include headaches, drowsiness, depression, dizziness, vertigo, confusion, paresthesias, dysarthria, hyperirritability, psychosis, convulsions, and shaking (tremors).

SUMMARY OF THE INVENTION

The present disclosure is based, at least in part, on the development of enteric formulations comprising cycloserine compounds, which exhibited superior, unexpected features, for example, stable under moisture and/or acidic environments (e.g., gastrointestinal tract), superior dissolution efficiency at a neutral pH condition (e.g., pH 6.8), and/or enhanced bioavailability.

Accordingly, one aspect of the present disclosure provides a solid dosage form, comprising: (i) an inner core, which comprises a cycloserine compound and a pharmaceutically acceptable excipient, (ii) an enteric layer coated (e.g., directly or indirectly) on the inner core; and optionally (iii) an isolation layer between the inner core and the enteric layer. The pharmaceutically acceptable excipient may comprise a filler, a binder, a disintegrating agent, a lubricant, or a mixture thereof. Alternatively or in addition, the enteric layer comprises polymethacrylate, phthalate, cellulose ester, shellac, alginate, or a mixture thereof. The isolation layer comprises a cellulose polymer, for example, hydroxypropyl methylcellulose (HPMC). In some embodiments, the solid dosage form contains about 10 mg to about 1500 mg of the cycloserine compound. In some embodiments, the cycloserine compound (e.g., D-cycloserine, L-cycloserine, or a pharmaceutically salt thereof) can be in particle form having a D90 value ranging from about 0.05 μm to about 500 μm.

In some embodiments, the pharmaceutical excipients in the inner core of the solid dosage form may comprise one or more fillers, one or more binders, one or more disintegrating agent, and/or one or more lubricant. Examples of fillers include starch, lactose, sucrose, glucose, mannitol, calcium phosphate, microcrystalline cellulose, or a mixture thereof. Examples of binders include carboxymethylcellulose, microcrystalline cellulose (MCC) (e.g., MCC pH 102 or MCC pH 112), hydroxypropyl cellulose, alginates, gelatin, polyvinylpyrrolidinone, acacia, or a mixture thereof. Exemplary disintegrating agents include agar, calcium carbonate, potato or tapioca starch, alginic acid, certain silicates, sodium starch glycolate (SSG), croscarmellose, crospovidone, sodium carbonate, or a mixture thereof. Exemplary lubricants include magnesium stearate, colloidal silicon dioxide, talc, calcium stearate, solid polyethylene glycol, sodium lauryl sulfate, or a mixture thereof.

In some examples, the pharmaceutically acceptable excipient in the inner core may comprise about 50-500 mg of the filler, about 10-100 mg of the binder, about 10-200 mg of the disintegrating agent, and about 5-100 mg of the lubricant. In some examples, the solid dosage described herein may comprise a filler, which comprises MCC pH 102, a binder, which comprises hydroxylpropyl cellulose (HPC), a disintegrating agent, which comprises croscarmellose, and a lubricant, which comprises magnesium stearate.

In some embodiments, the enteric layer of the solid dosage form may comprise: (a) polymethacrylate, which can be poly(methacrylic acid-co-ethyl acrylate) in a molar ratio of 1:1, poly(methacylic acid-co-methyl methacrylate) in a molar ratio of 1:1, poly(methacylic acid-co-methyl methacrylate) in a molar ratio of 1:2, or poly(methyl acrylate-co-methyl methacrylate-co-methacrylic acid) in a molar ratio of 7:3:1; (b) phthalate, which can be polyvinyl acetate phthalate, hydroxypropyl methylcellulose phthalate, diethyl phthalate, or cellulose acetate phthalate; and/or (c) cellulose ester, which can be cellulose acetate trimellitate, cellulose acetate succinate, or hydroxypropyl methylcellulose acetate succinate. In some examples, the enteric layer may comprise 90.5%-98.49% of poly(methacrylic acid-co-ethyl acrylate) in a ratio of 1:1 by weight, 0.5%-2% of sodium lauryl sulfate by weight, 0.01%-2.5% of triethyl citrate by weight, 0.5%-2.5% of colloidal silicon dioxide by weight, and 0.5%-2.5% of talc by weight.

In some embodiments, the isolation layer may comprise hydroxypropyl methylcellulose (HPMC), which may have an average molecular weight of 50,000 to 125,000 Dalton. In some examples, the isolation layer comprises 95.5%-99.49% of hydroxypropyl methylcellulose by weight, 0.5%-2.5% of talc by weight, and 0.01%-2% of triacetin by weight.

In some embodiments, the solid dosage form of claim 2, which comprises about 10 mg to about 300 mg of the enteric layer and/or about 10 mg to about 100 mg of the isolation layer.

In one example, the solid dosage form described herein comprises (a) an inner core that comprises a cycloserine compound (e.g., D-cycloserine, L-cycloserine, or a pharmaceutically acceptable salt thereof) and a pharmaceutically acceptable excipient, which comprises MCC pH 102, croscarmellose, HPC, and magnesium stearate; (b) an enteric layer, which comprises polymethacrylate; and (c) an isolation layer, which comprises HPMC having a molecular weight of 50,000 to 125,000 Dalton. The isolation layer is located between the inner core and the enteric layer.

Any of the solid dosage form described herein may be a pharmaceutical composition, a nutraceutical composition, a health food, or a medical food.

In another aspect, the present disclosure provides a method for alleviating a symptom associated with a neuropsychiatric disease or tuberculosis, the method comprising administering to a subject in need thereof (e.g., a human patient) an effective amount of any of the solid dosage forms described herein. Exemplary neuropsychiatric disorders include schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

In some embodiments, the solid dosage form is administered to the subject three times a day to one time every three months. In some embodiments, the subject is on an additional treatment for the neuropsychiatric disorder or on an additional treatment of tuberculosis. In some embodiments, the method may further comprise administering to the subject an additional therapeutic agent for treating the neuropsychiatric disorder or tuberculosis.

Also within the scope of the present disclosure are any of the solid dosage forms described herein for use in treating a neuropsychiatric disease as described herein or tuberculosis; or for manufacturing a medicament for use in treating the target disorder.

The details of one or more embodiments of the disclosure are set forth herein. Other features, objects, and advantages of the disclosure will be apparent from the Detailed Description, the Examples, and the Claims.

DETAILED DESCRIPTION

The present disclosure is based, at least in part, on the development of solid cycloserine compound formulations, which exhibit superior features such as stability under acidic environment, efficient dissolution at neutral pH, and/or high bioavailability. As such, the solid formulations described herein would significantly enhance treatment efficacy of cycloserine compound for neuropsychiatric disorders and bacterial infection such as tuberculosis.

Accordingly, provided herein are solid dosage forms of cycloserine compounds and uses thereof in treating the target diseases as described herein or alleviating one or symptoms thereof.

Formulations of Cycloserine Compounds

The formulation (e.g., solid formulation) of cycloserine compounds as disclosed herein may comprise an inner core that contains a cycloserine compound (an active ingredient) and an enteric layer, which may be coated on the inner core directly or indirectly. In some instances, the formulation may further comprise an isolation layer, which may be located between the inner core and the enteric layer.

The inner core may comprise a cycloserine compound and a pharmaceutically acceptable carrier or excipient. The term "cycloserine compound" refers to cycloserine (in D- or L form or a racemic mixture of the DL-form pharmaceutically acceptable salts or esters thereof, or functional derivatives thereof. In some embodiments, a cycloserine compound can be nano-crystalline D-cycloserine. In some embodiments, a cycloserine compound can be nano-crystalline L-cycloserine. In other embodiments, a cycloserine compound can be a racemic mixture of DL-cycloserine in nano-crystalline form. The chemical structure of cycloserine is provided below:

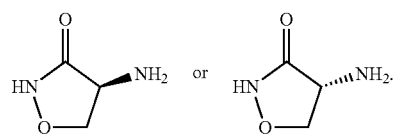

A functional derivative of cycloserine can be a compound having the same core structure of cycloserine with one or more substituents, for example, alkyl, alkenyl, alkynyl, and/or a halogen.

In some instances, a cycloserine compound is a pharmaceutically acceptable salt of cycloserine. The pharmaceutically acceptable salt can be either an inorganic salt or an organic salt. The term "salt" refers to ionic compounds that result from the neutralization reaction of an acid and a base. A salt is composed of one or more "cations" (positively charged ions) and one or more "anions" (negatively charged ions) so that the salt is electrically neutral (without a net charge). Salts described herein may include those derived from suitable organic acids as disclosed herein, for example, dicarboxylic acids. Examples of organic and inorganic acids include but not limited to acetic acid, ascorbic acid, aspartic acid, benzoic acid, formic acid, fumaric acid, galic acid, gluconic acid, lactic acid, lauric acid, methansulfonic acid, niconitic acid, oxalic acid, oxalic acid, maleic acid, malonic acid, L-tartaric acid, D-tartaric acid, meso-tartaric acid, malic acid, citric acid, succinic acid, stearic acid, pentetic acid, propinoic acid, p-toluenesulfonic acid, undecanoic acid, valeric acid, ethylenediaminetetraacetic acid, boric acid, hydrochloric acid, hydrobromic acid, chromic acid, nitric acid, phosphoric acid, phosphorous acid, hypophosphorus acid, sulfuric acid, and sulfonic acid.

In some examples, a salt of the cycloserine compound has the formula [A][B], in which [A] is a cation form of a cycloserine compound and [B] is an anion form of a compound of formula (I):

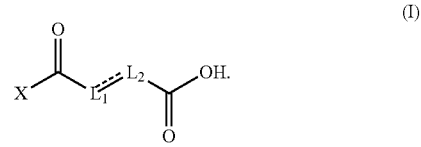

In formula (I):

X is —NH$_2$ or —OH;

each of $L_1$ and $L_2$, independently, is $C_{1-6}$ alkylene, $C_{2-6}$ alkenylene, or $C_{2-6}$ alkynylene, or one of $L_1$ and $L_2$ is N, O, or S, and the other one is $C_{1-6}$ alkylene, $C_{2-6}$ alkenylene, or $C_{2-6}$ alkynylene, as valency permits;

⸺ is either a single or double bond; and the ratio of [A] and [B] in the salt ranges from 10:1 to 1:10.

In some embodiments, X is —$NH_2$. In some embodiments, X is —OH.

In some embodiments, each of $L_1$ and $L_2$, independently, is $C_{1-6}$ alkylene, $C_{2-6}$ alkenylene, or $C_{2-6}$ alkynylene, or one of $L_1$ and $L_2$ is N, O, or S, and the other one is $C_{1-6}$ alkylene, $C_{2-6}$ alkenylene, or $C_{2-6}$ alkynylene, as valency permits. In some embodiments, each of $L_1$ and $L_2$, independently, is $C_{1-6}$ alkylene, $C_{2-6}$ alkenylene, or $C_{2-6}$ alkynylene, wherein each of $C_{1-6}$ alkylene, $C_{2-6}$ alkenylene, or $C_{2-6}$ alkynylene. In some embodiments, each of $L_1$ and $L_2$, independently, is $C_{1-6}$ alkylene, $C_{2-6}$ alkenylene, or $C_{2-6}$ alkynylene. In some embodiments, one of $L_1$ and $L_2$ is N, O, or S, and the other one is $C_{1-6}$ alkylene, $C_{2-6}$ alkenylene, or $C_{2-6}$ alkynylene, as valency permits. In some embodiments, at least one of $L_1$ and $L_2$ is $C_{1-6}$ alkylene, $C_{2-6}$ alkenylene, or $C_{2-6}$ alkynylene. As disclosed herein, $C_{1-6}$ alkylene, $C_{2-6}$ alkenylene, or $C_{2-6}$ alkynylene can be either unsubstituted or optionally substituted with halogen, —CN, —$NO_2$, —OH, —O($C_{1-6}$ alkyl), —$NH_2$, or —$N_3$.

In some embodiments, at least one of $L_1$ and $L_2$ is $C_{1-6}$ alkylene, which may be substituted or unsubstituted $C_{1-6}$ alkylene. In some embodiments, at least one of $L_1$ and $L_2$ is methylene, which may be substituted or unsubstituted methylene. In some embodiments, at least one of $L_1$ and $L_2$ is methylene. As used herein, methylene can be either unsubstituted or optionally substituted with halogen, —CN, —$NO_2$, —OH, —O($C_{1-6}$ alkyl), or —$NH_2$. In some embodiments, at least one of $L_1$ and $L_2$ is methylene. In some embodiments, each of $L_1$ and $L_2$ is methylene substituted with halogen, —CN, —$NO_2$, —OH, —O($C_{1-6}$ alkyl), or —$NH_2$. In some embodiments, each of $L_1$ and $L_2$ is methylene substituted with —OH. In some embodiments, at least one of $L_1$ and $L_2$ is unsubstituted methylene. In some embodiments, both $L_1$ and $L_2$ are methylene, which both may be substituted methylene or both may be unsubstituted methylene. In some embodiments, at least one of $L_1$ and $L_2$ is $C_{2-6}$ alkenylene, which may be substituted or unsubstituted $C_{2-6}$ alkenylene. In some embodiments, at least one of $L_1$ and $L_2$ is $C_{2-6}$ alkynylene, which may be substituted or unsubstituted $C_{2-6}$ alkynylene.

In some embodiments, X is —OH; and ⸺ is a single bond. In some embodiments, X is —OH; ⸺ is a single bond; and each of $L_1$ and $L_2$ is methylene substituted with —OH. In some embodiments, X is —OH; ⸺ is a double bond; and each of $L_1$ and $L_2$ is optionally substituted methylene.

In some embodiments, at least one of $L_1$ and $L_2$ is N, O, or S, and the other one is $C_{1-6}$ alkylene, $C_{2-6}$ alkenylene, or $C_{2-6}$ alkynylene, as valency permits. In some embodiments, at least one of $L_1$ and $L_2$ is N and the other one is $C_{1-6}$ alkylene, $C_{2-6}$ alkenylene, or $C_{2-6}$ alkynylene, as valency permits. In some embodiments, at least one of $L_1$ and $L_2$ is substituted N and the other one is $C_{1-6}$ alkylene, $C_{2-6}$ alkenylene, or $C_{2-6}$ alkynylene, as valency permits. In some embodiments, at least one of $L_1$ and $L_2$ is O and the other one is $C_{1-6}$ alkylene, $C_{2-6}$ alkenylene, or $C_{2-6}$ alkynylene, as valency permits. In some embodiments, at least one of $L_1$ and $L_2$ is S and the other one is $C_{1-6}$ alkylene, $C_{2-6}$ alkenylene, or $C_{2-6}$ alkynylene, as valency permits.

In some embodiments, ⸺ is a single bond. In some embodiments, ⸺ is a double bond.

In some embodiments, the ratio of [A] and [B] in the salt ranges from 10:1 to 1:10, 9:1 to 1:9, 8:1 to 1:8, 7:1 to 1:7, 6:1 to 1:6, 5:1 to 1:5, 4:1 to 1:4, 3:1 to 1:3, 2:1 to 1:2, or 2:1 to 1:1, wherein [A] is a cation form of a cycloserine compound and [B] is an anion form of a compound of formula (I):

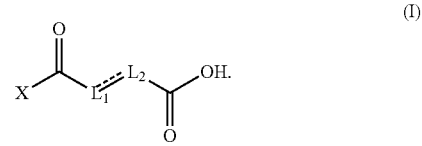

In some embodiments, the ratio of [A] and [B] in the salt ranges from 10:1 to 1:10. In some embodiments, the ratio of [A] and [B] in the salt ranges from 9:1 to 1:9. In some embodiments, the ratio of [A] and [B] in the salt ranges from 8:1 to 1:8. In some embodiments, the ratio of [A] and [B] in the salt ranges from 7:1 to 1:7. In some embodiments, the ratio of [A] and [B] in the salt ranges from 6:1 to 1:6. In some embodiments, the ratio of [A] and [B] in the salt ranges from 5:1 to 1:5. In some embodiments, the ratio of [A] and [B] in the salt ranges from 4:1 to 1:4. In some embodiments, the ratio of [A] and [B] in the salt ranges from 3:1 to 1:3. In some embodiments, the ratio of [A] and [B] in the salt ranges from 2:1 to 1:2. In some embodiments, the ratio of [A] and [B] in the salt ranges from 2:1 to 1:1. In some embodiments, the ratio of [A] and [B] in the salt is 7:1, 6:1, 5:1, 4:1, 3:1, 2:1, or 1:1.

In some embodiments, the cycloserine compound is of formula:

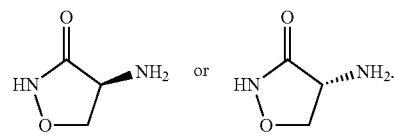

In some embodiments, the cycloserine compound is:

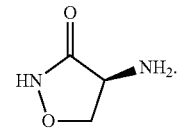

In some embodiments, the cycloserine compound is:

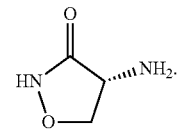

In some embodiments, the compound of formula (I) is of formula:

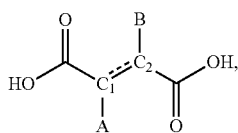
(Ia)

wherein each of A and B, independently, is —NH$_2$, —OH, or H; and
C$_1$⚏C$_2$ is C$_1$-C$_2$ or C$_2$=C$_1$.

In some embodiments, at least one of A and B is —NH$_2$. In some embodiments, at least one of A and B is —OH. In some embodiments, A and B are both —OH. In some embodiments, the compound of formula (I) is succinic acid, D-tartaric acid, L-tartaric acid, meso-tartaric acid, fumaric acid, maleic acid, or malic acid.

In some embodiments, the compound of formula (Ia) is of formula:

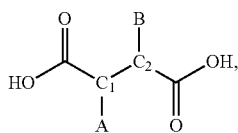
(Ib)

wherein each of A and B, independently, is —OH or —H. In some embodiments, at least one of A and B is —OH. In some embodiments, A and B are both —OH.

In some embodiments, the compound of formula (Ib) is:

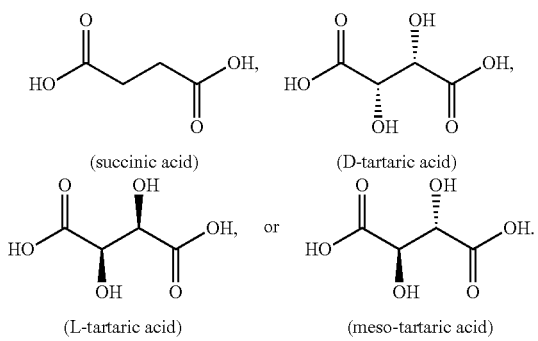

(succinic acid) (D-tartaric acid)

(L-tartaric acid) (meso-tartaric acid)

In some embodiments, the compound of formula (Ib) is selected from the group consisting of: succinic acid, D-tartaric acid, and L-tartaric acid. In some embodiments, the compound of formula (Ib) is selected from the group consisting of: succinic acid, D-tartaric acid, L-tartaric acid, and meso-tartaric acid, and the ratio between [A] and [B] ranges from 5:1 to 1:1. In some embodiments, the compound of formula (Ib) is

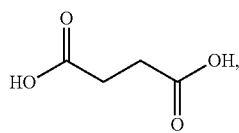

and the ratio between [A] and [B] is 4:1. In some embodiments, the compound of formula (Ib) is

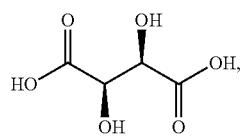

and the ratio between [A] and [B] is 2:1. In some embodiments, the compound of formula (Ib) is

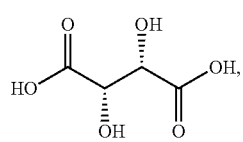

and the ratio between [A] and [B] is 1:1.

In some embodiments, the compound of formula (Ia) is a compound of formula (Ic):

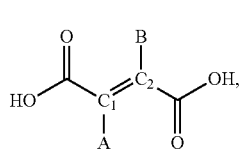
(Ic)

wherein each of A and B, independently, is —OH or —H. In some embodiments, at least one of A and B is —OH. In some embodiments, A and B are both —OH.

In some embodiments, the compound of formula (Ic) is selected from

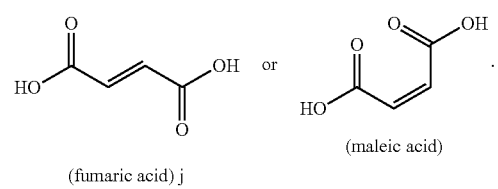 [SMILES: O=C(O)/C=C/C(=O)O ; "or" ; O=C(O)/C=C\C(=O)O ; "."]

(fumaric acid) (maleic acid)

In some embodiments, the compound of formula (Ic) is fumaric acid. In some embodiments, the compound of formula (Ic) is maleic acid. In some embodiments, the compound of formula (Ic) is

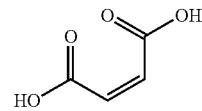

and the ratio between [A] and [B] described herein is 1:1.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ to alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

Alkyl, alkenyl, and alkynyl groups, which are divalent bridging groups, are further referred to using the suffix -ene, e.g., alkylene, alkenylene, and alkynylene.

The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

The cycloserine compound in the solid formulation disclosed herein may be in particle form, for example, having a D90 value ranging from about 0.05-500 µm (e.g., about 0.05-300 µm, about 0.05 to 200 µm, about 0.05-100 µm, about 0.05 to 50 µm, about 0.05-20 µm, about 0.05-10 µm, about 0.05-5 µm, about 0.05-2 µm, about 0.05-1 µm, about 5-200 µm, about 100-300 µm, or about 100-250 µm). D-values ($D_{10}$, $D_{50}$ or $D_{90}$) are commonly used to reflect particle size (diameter) distribution in a population. The $D_{90}$ value refers to ≥90% of the particles in the population having a diameter falling in the ranges noted above.

The pharmaceutically acceptable carrier or excipient in the inner core of the solid formulation disclosed herein may comprise a filler, a binder, a disintegrating agent, a lubricant, or a combination thereof. Exemplary fillers include, but are not limited to, lactose, microcrystalline cellulose, calcium hydrogen phosphate, or a mixture thereof. Microcrystalline cellulose can be used as a stabilizing and anti-moisture agent, which can be replaced with cellulose's derivatives, starch, calcium phosphate dibasic anhydrous and mixtures thereof.

Exemplary binders include, but are not limited to, pregelatinised maize starch, polyvinylpyrrolidone, hydroxypropyl methylcellulose, carboxymethylcellulose, microcrystalline cellulose (MCC), hydroxypropyl cellulose, alginates, gelatin, acacia, or a mixture thereof.

Exemplary lubricants include, but are not limited to, magnesium stearate, talc, silica, colloidal silicon dioxide, calcium stearate, solid polyethylene glycol, sodium lauryl sulfate, or a mixture thereof. Exemplary disintegrating agents (disintegrants) include, but are not limited to, agar, calcium carbonate, potato or tapioca starch, alginic acid, certain silicates, sodium starch glycolate (SSG), croscarmellose, crospovidone, sodium carbonate, or a mixture thereof.

In some instances, the pharmaceutically acceptable carrier may also comprise one or more of the followings: wetting agents (e.g., sodium lauryl sulphate, cetyl alcohol, and glycerol monostearate); solution retarding agents (e.g., paraffin); absorption accelerators (e.g., quaternary ammonium compound); and absorbents (e.g., kaolin and bentonite clay). Alternatively or in addition, the solid formulation may also contain sodium citrate and/or dicalcium phosphate. In some instances, the solid formulation may comprise inert diluents, dispersing and/or granulating agents, surface active agents and/or emulsifiers, preservatives, buffering agents and/or pH adjusters, sustained release reagents, anti-sedimentation agents, oils, or mixtures thereof. Excipients such as cocoa butter and suppository waxes, coloring agents, coating agents, sweetening, flavoring, and perfuming agents may also be present in the composition.

The solid dosage form of cycloserine described herein may comprise an enteric layer composed of one or more enteric materials. In some instances, the solid dosage form may contain about 10 to 500 mg (e.g., about 30-400 mg, about 30-300 mg, about 30-200 mg, about 30-150 mg, about 50-150 mg, about 50 mg-125 mg, or about 75-100 mg) of the enteric materials. Enteric layer or enteric coating typically refers to a polymer-based barrier coated on oral medication that prevents dissolution or disintegration of the medication in the gastric environment.

Exemplary enteric materials for use in making the solid dosage form described herein include polymethacrylate-based coating material, phthalate-based coating material, cellulose ester-based coating material, shellac, sodium alginate, or a mixture thereof.

In some embodiments, the polymethacrylate-based coating material can be poly(methacrylic acid-co-ethyl acrylate) in a molar ratio of 1:1 (i.e. Eudragit L 100-55, Eudragit L 30 D-55, Eastacryl 30 D series, Kollicoat MAE 30 DP, Kollicoat MAE 100 P, Acryl-EZE 93 series and Acryl-EZE MP series), poly(methacylic acid-co-methyl methacrylate) in a molar ratio of 1:1 (i.e. Eudragit L 100, Eudragit L 12,5, Eudragit L 12,5 P, and Opadry 94 series), poly(methacylic acid-co-methyl methacrylate) in a molar ratio of 1:2 (i.e. Eudragit S 100, Eudragit S 12,5, Eudragit S 12,5 P, and Opadry 95 series), and poly(methyl acrylate-co-methyl methacrylate-co-methacrylic acid in a molar ratio of 7:3:1 (i.e. Eudragit FS 30 D).

In some embodiments, the phthalate-based coating material can be polyvinyl acetate phthalate (i.e. Opadry 91 series, and Sureteric series), hydroxypropyl methylcellulose phthalate (i.e. HPmcp-HP Grades series), diethyl phthalate, and cellulose acetate phthalate (i.e. Eastman™ C-A-P).

In some embodiments, the cellulose ester-based coating material can be cellulose acetate trimellitate, cellulose acetate succinate, and hydroxypropyl methylcellulose acetate succinate (i.e. AQOAT AS series, and ENTER-ACT™ HPMCAS).

In some examples, the enteric materials in the solid dosage form may comprise (by weight) 90.5%-98.49% of poly(methacrylic acid-co-ethyl acrylate) in a molar ratio of 1:1, 0.5%-2% of sodium lauryl sulfate, 0.01%-2.5% of triethyl citrate, 0.5%-2.5% of colloidal silicon dioxide, and 0.5%-2.5% of talc. In some embodiments, the amount of poly(methacrylic acid-co-ethyl acrylate) in a molar ratio of 1:1 in enteric layer can be (by weight) 91%-98%, 92%-97.5%, 93%-97%, 94%-96.5%, 95%-96%, or 95%-95.5%.

In some embodiments, the solid dosage form described herein may further comprise an isolation layer, which may be located between the inner core and the enteric layer. The isolation layer may comprise materials such as hydroxypropyl methylcellulose-based coating materials. In some examples, the average molecular weight of the hydroxypropyl methylcellulose can be about 50,000 dalton to 125,000 dalton. Other commercially available isolation layer materials can also be used in the solid dosage form described herein. In one example, a solid dosage form may contain about 10-100 mg of the isolation layer, for example, about 15-95 mg, about 15-80 mg, about 20-60 mg, about 20-50 mg, about 25-40 mg or about 25-30 mg. In one example, the isolation layer may comprise (by weight) 95.5%-99.49% of hydroxypropyl methylcellulose, 0.5%-2.5% of talc, and 0.01%-2% of triacetin. In some embodiments, the amount of hydroxypropyl methylcellulose comprised in the isolation layer can be (by weight) 96%-99%, or 97%-98%.

In certain embodiments, the solid dosage form described herein may contain about 10 to 1500 mg, about 50 to 1000 mg, about 100 to 800 mg, 250 to 600 mg, 300 to 550 mg, 350 to 500 mg, or 400 to 450 mg of a cycloserine compound (e.g., D-cycloserine or an acceptable salt thereof as described herein). The cycloserine compound may be mixed with pharmaceutically acceptable excipients containing about 50-500 mg of a filler (e.g., MCC pH 102), about 10-100 mg of a binder (e.g., HPC), about 10-200 mg of a disintegrating agent (e.g., croscarmellose), and about 5-100 mg of a lubricant (e.g., magnesium stearate).

The solid dosage form described herein may further contain one or more enteric materials as those described herein in an amount of about 50 to 150 mg, about 50 to 100 mg, about 55 to 95 mg, about 60 to 90 mg, about 65 to 85 mg, about 70 to 80 mg, or about 70 to 75 mg. The enteric materials may comprise (by weight) 90.5%-98.49% of poly (methacrylic acid-co-ethyl acrylate) in a molar ratio of 1:1, 0.5%-2% of sodium lauryl sulfate, 0.01%-2.5% of triethyl citrate, 0.5%-2.5% of colloidal silicon dioxide, and 0.5%-2.5% of talc.

Optionally, the solid dosage form may further comprise an isolation layer of about 10-50 mg of the isolation layer, for example, about 15-45 mg, about 20-35 mg, about 25-30 mg, or about 35-40 mg. The isolation layer may comprise (by weight) 95.5%-99.49% of hydroxypropyl methylcellulose, 0.5%-2.5% of talc, and 0.01%-2% of triacetin.

In some embodiments, the solid formulation disclosed herein is in a dosage form (also known as a unit dose), which refers to compositions ready for delivering to subjects in need of the treatment via a suitable route. A dosage form typically contains a mixture of active ingredients and inactive components (excipients) in a particular configuration (e.g., tablet, capsule, transdermal pad, granule, powder, sachet, etc.) and apportioned into a particular dose. A "unit dose" is a discrete amount of the pharmaceutical composition comprising a predetermined amount of the active ingredient. The amount of the active ingredient is generally equal to the dosage of the active ingredient, which would be administered to a subject and/or a convenient fraction of such a dosage, such as one-half or one-third of such a dosage.

The solid dosage forms described herein may be for oral administration and may be in form of a capsule or a tablet. All commercially available capsules can be used here for making the solid dosage form, including hard and soft gelatin capsules, HPMC capsules, and the like. Exemplary materials, including commercially available ones, for making the capsule include, but are not limited to, hydroxypropyl methylcellulose (HPMC), gelatin, methyl paraben (i.e., methyl-4-hydroxybenzoate), propyl paraben (i.e., propyl-4-hydroxybenzoate), sodium lauryl sulphate, Brilliant Blue FCF, new coccin, titanium dioxide, Sunset Yellow FCF, tartrazine, water, or combination thereof.

In some embodiments, the capsule formulation may further comprise an enteric coating on the surface of the capsule. All commercially available enteric coating can be applied on the surface of the capsule for the capsule formulation described herein. In some examples, the enteric coating can be composed of copolymers of methacrylic acid and ethyl acrylate, e.g., Kollicoat® MAE 30 DP (BASF). In some instances, the molar ratio of methacrylic acid and ethyl acrylate in the copolymer is 1:1 and the solid content is 30% (by weight). In some examples, the enteric coating may comprise the same enteric materials disclosed herein. For the coating purpose, the material of the enteric coating can be resolved in an organic solvent, for example, propylene glycol.

Alternatively, the solid dosage forms described herein may be for topical administration, which may be in the form of a transdermal patch. For example, the cycloserine compound-containing pharmaceutical composition as described herein may be spread on an impermeable support to obtain a patch. In some examples, the impermeable support is a support for a matrix system (e.g., matrix-dispersion system and drug in-adhesive), a reservoir patch system or a microreservoir system.

Relative amounts of the cycloserine compound, the pharmaceutically acceptable excipient, the isolation layer and enteric layer materials, and/or any additional ingredients in the compositions described herein may vary, depending upon the identity, size, and/or condition of the subject treated and further depending upon the route by which the composition is to be administered. The composition may comprise between 0.1% and 99.5% (w/w) active ingredient.

Compositions comprising cycloserine compounds such as any of the solid form disclosed herein may be a pharmaceutical composition, a nutraceutical composition, a health food or health food product, or a medical food.

In certain embodiments, the compositions described herein can be a health food or a health food product. The terms "health food" or "health food product" refers to any kind of liquid and solid/semi-solid materials that are used for nourishing humans and animals, for improving basic behavioral functioning, hyperactivity, anxiety, depression, suicidal ideation and/or behavior sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods.

The healthy food or healthy food product can be any kinds of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, or for facilitating treatment of any of the target diseases noted herein (e.g., a neuropsychiatric disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation. Such liquid form healthy food product may be prepared by dissolving any of the solid dosage formulations disclosed herein in a suitable solution.

The health food product described herein, may comprise one or more edible carriers in addition to the active ingredient. The edible carriers may confer one or more of the benefits to the product as described herein. Examples of edible carriers include starch, cyclodextrin, maltodextrin, methylcellulose, carbon methoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the health food products described herein may further include neuroprotective foods, such as fish oil, flax seed oil, and/or benzoate.

In some examples, the health food product is a nutraceutical composition, which refers to compositions containing components from food sources and conferring extra health benefits in addition to the basic nutritional value found in foods. A nutraceutical composition as described herein may comprises the cycloserine compound as an active ingredient and other components described herein, e.g., pharmaceutically acceptable carrier or excipient, enteric layer, and/or isolation layer, which would promote good health and/or enhance stability and bioactivity of the cycloserine compound.

The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration.

In certain embodiments, the composition (e.g., the solid formulation described herein) is a medical food. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management). In some examples, a medical food composition described herein is not one of those that would be simply recommended by a physician as part of an overall diet to manage the symptoms or reduce the risk of a disease or condition.

In some embodiments, the medical food composition described herein may comprise at least one component, which can be either naturally-occurring or synthetic (non-naturally occurring), would confer one or more benefits to the cycloserine compound in the composition, for example, stability, bioavailability, and/or bioactivity. Any of the carriers, enteric materials, and/or isolation layer described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

Any of the compositions such as solid form formulations described herein may contain an effective amount of a cycloserine compound. An "effective amount" of the cycloserine compound described herein refers to an amount sufficient to elicit the desired biological response, i.e., treating the condition. As will be appreciated by those of ordinary skill in this art, the effective amount of the cycloserine described herein may vary depending on such factors as the desired biological endpoint, the pharmacokinetics of the cycloserine compound, the condition being treated, the mode of administration, and the age and health of the subject. In certain embodiments, an effective amount is a therapeutically effective amount. In certain embodiments, an effective amount is a prophylactic effective amount.

The compositions such as solid dosage forms may be suitable for human use. Such compositions may also be suitable for use in animals. Modification of pharmaceutical compositions suitable for administration to humans in order to render the compositions suitable for administration to various animals is well understood, and the ordinarily skilled veterinary pharmacologist can design and/or perform such modification with ordinary experimentation.

Pharmaceutical compositions described herein can be prepared by any method known in the art of pharmacology. In general, such preparatory methods include bringing a cycloserine compound such as D-cycloserine or an acceptable salt thereof described herein (i.e., the "active ingredient") into association with one or more carriers or excipients (e.g. isolation layer and/or enteric layer materials), and/or one or more other accessory ingredients, and then, if necessary and/or desirable, shaping, and/or packaging the product into a desired single- or multi-dose unit.

The composition described herein can be formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

In the case of capsules, the active ingredient can be encapsulated into capsule shells. In some instances, the active ingredient as disclosed herein is not mixed with any excipient or carrier. In other instances, the active ingredient is mixed with suitable excipients or carriers as disclosed herein. Any of the enteric layers disclosed herein may be coated on the surface of the capsule shell.

Solid compositions of a similar type (e.g., the inner core as disclosed herein) can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as isolation layer coating, enteric coatings, release controlling coatings, and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but not limited to, polymeric substances and waxes.

Kits

Also encompassed by the disclosure are kits (e.g., pharmaceutical packs), which may comprise a pharmaceutical composition such as a solid dosage form described herein and a container (e.g., a vial, ampule, bottle, syringe, and/or dispenser package, or other suitable container) for placing the composition. Such kits may be useful in treating and/or reducing the risk for a neuropsychiatric disorder or tuberculosis in a subject in need thereof.

In certain embodiments, a kit described herein may further include instructions for using the composition described herein included in the kit. A kit described herein may also include information as required by a regulatory agency such as the U.S. Food and Drug Administration (FDA). In certain embodiments, the information included in the kits is prescription information. In certain embodiments, the kits and instructions provide for treating and/or reducing the risk for a neuropsychiatric disorder or tuberculosis.

A kit described herein may include one or more additional pharmaceutical agents described herein as a separate composition.

Method of Treatment

Any of the compositions (e.g., solid dosage form) comprising a cycloserine compound may help achieve short-term or long-term health objectives in patients having improve basic behavioral functioning, hyperactivity, anxiety, depression, suicidal ideation and/or behavior, sensorimotor gating, pain threshold, memory and/or cognitive functioning in, e.g., human subjects who have or are at risk for a neuropsychiatric disorder.

Accordingly, also provided herein are methods for treating a neuropsychiatric disorder (e.g., a central nervous system disorder) or a bacterial infectious disease (e.g., tuberculosis) in a subject in need of the treatment, by administering to the subject an effective amount of the composition (e.g., solid dosage form) described herein. An effective amount of the composition may be a therapeutically effective amount or a prophylactically effective amount.

A "therapeutically effective amount" of the composition described herein is an amount sufficient to provide a therapeutic benefit in the treatment of a condition or to delay or minimize one or more symptoms associated with the condition. A therapeutically effective amount of the composition described herein means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In some instances, the amount of the cycloserine compound in the composition is effective in modulating N-methyl-D-aspartate receptor a in a subject with neuropsychiatric disorder.

A "prophylactically effective amount" of the composition described herein is an amount sufficient to prevent a condition, or one or more symptoms associated with the condition or prevent its recurrence. A prophylactically effective amount of the composition described herein means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS disorders, or refers to a disorder that involves either psychiatric symptoms or syndromes caused by organic brain disorders. The main characteristics of neuropsychiatric symptoms include occurrence of the various psychiatric symptoms, cognitive impairment, neurological symptoms or the possibility of early cerebral development symptoms.

In some embodiments, the neuropsychiatric disorder can be schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, or chronic pain syndromes.

The compositions described herein are useful in treating and/or preventing a neuropsychiatric disorder or bacterial infection such as tuberculosis. To perform the methods described herein, an effective amount of the solid dosage form may be administered to a subject in need of the treatment via a suitable route (e.g., oral administration or topical administration). The exact amount of the cycloserine compound such as D-cycloserine or an acceptable salt thereof described herein required to achieve an intended effect may vary from subject to subject, depending, for example, on species, age, and general condition of a subject, severity of the side effects or disorder, identity of cycloserine compound described herein, mode of administration, and the like.

An effective amount of the cycloserine compound may be included in a single dose (e.g., single oral dose) or in multiple doses (e.g., multiple oral doses). In certain embodiments, when multiple doses are administered to a subject, any two doses of the multiple doses may include different or substantially the same amounts of the cycloserine compound described herein. The composition comprising a cycloserine compound may be given to the subject at a frequency of three times a day to one time every three months. In certain embodiments, the composition comprising a cycloserine compound may be given to the subject at a frequency of two times a day to one time every month. In certain embodiments, the composition comprising a cycloserine compound may be given to the subject at a frequency of one time a day to one time every week.

In certain embodiments, when multiple doses are administered to a subject, the frequency of administering the multiple doses to the subject can be three doses a day, two doses a day, one dose a day, one dose every other day, one dose every third day, one dose every week, one dose every other week, one dose monthly one dose every other month, or one dose every three months. In certain embodiments, the frequency of administering the multiple doses to the subject or applying the multiple doses to the tissue or cell is one dose per day. In certain embodiments, the frequency of administering the multiple doses to the subject can be two doses per day When multiple doses are administered to a subject, the duration between the first dose and last dose of the multiple doses can be 4 hours, 8 hours, 12 hours, 24 hours, one day, two days, four days, one week, two weeks, three weeks, one month, two months, three months, four months or six months.

In certain embodiments, a single dose of the cycloserine compound such as D-cycloserine or a pharmaceutically acceptable salt thereof may be between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive. In certain embodiments, a dose of the cycloserine compound may be between 100 mg and 1500 mg, inclusive, or between 300 mg and 1000 mg, inclusive.

Dose ranges as described herein may be for use in adult human patients. The amount to be administered to, for example, a child or an adolescent can be determined by a medical practitioner or person skilled in the art and can be lower or the same as that administered to an adult.

The composition described herein can be administered in combination with one or more additional pharmaceutical agents (e.g., therapeutically and/or prophylactically active agents) useful in treating and/or reducing the risk for a neuropsychiatric disorder or bacterial infection such as tuberculosis. The composition can be administered in combination with one or more additional pharmaceutical agents that improve the activity (e.g., activity (e.g., potency and/or efficacy) in treating and/or reducing the risk for a neuropsychiatric disorder or tuberculosis in a subject in need thereof, improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects.

The composition (e.g., the solid dosage form) described herein can be administered concurrently with, prior to, or subsequent to the one or more additional pharmaceutical agents for treating the target disease.

The additional pharmaceutical agents, which include prophylactically active agents, may be of any type, for example, small organic molecules, peptides, proteins (e.g., antibodies, nucleoproteins, lipoproteins, mucoproteins, glycoproteins), carbohydrates (e.g., monosaccharides, oligosaccharides, or polysaccharides)lipoproteins, small molecule-conjugated proteins such as antibody-drug conjugates (ADCs), steroids, nucleic acids (e.g., DNAs, RNAs, nucleotides, nucleosides, oligonucleotides such as antisense oligonucleotides), lipids, hormones, vitamins, and cells.

Each additional pharmaceutical agent may be administered at a dose and/or on a time schedule determined for that pharmaceutical agent. The additional pharmaceutical agents may also be administered together with each other and/or with the composition described herein in a single dose or administered separately in different doses. The particular combination to employ in a regimen will take into account compatibility of the composition described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent described herein can be an antipsychotic, an antidepressant, a psychostimulant, a mood stabilizer, an anxiolytic, an agent for treating attention deficit hyperactivity disorder (ADHD) or an agent for treating Alzheimer's disease (AD) or dementia.

Examples of antipsychotic drugs include, but not limited to, butyrophenone, haloperidol, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupentixol, thiothixene, zuclopenthixol, clozapine, norclozapine, olanzapine, risperidone, quetiapine, ziprasidone, amisulpride, asenapine, paliperidone, aripiprazole, lamotrigine, cannabidiol, LY2140023, droperidol, pimozide, butaperazine, carphenazine, remoxipride, piperacetazine, sulpiride, acamprosate, and tetrabenazine.

The antidepressants can be monoamine oxidase inhibitors (MAOIs), tricyclic antidepressants (TCAs), tetracyclic antidepressants (TeCAs), selective serotonin reuptake inhibitors (SSRIs), noradrenergic and specific serotonergic antidepressants (NASSAs), norepinephrine (noradrenaline) reuptake inhibitors, norepinephrine-dopamine reuptake inhibitors, serotonin-norepinephrine reuptake inhibitors (SNRIs), or serotonin-norepinephrine-dopamine reuptake inhibitors (SNDRIs). Examples of the antidepressants include, but not limited to, fluoxetine, paroxetine, escitalopram, citalopram, sertraline, fluvoxamine, venlafaxine, milnacipran, duloxetine, mirtazapine, mianserin, reboxetine, bupropion, amitriptyline, nortriptyline, protriptyline, desipramine, trimipramine, amoxapine, bupropion, clomipramine, desipramine, doxepin, isocarboxazid, tranylcypromine, trazodone, nefazodone, phenelzine, lamatrogine, lithium, topiramate, gabapentin, carbamazepine, oxcarbazepine, valproate, maprotiline, brofaromine, gepirone, moclobemide, isoniazid, and iproniazid.

In certain embodiments, the additional pharmaceutical agent is an agent for treating and/or reducing the risk for bacterial infection such as tuberculosis. Examples include, but are not limited to, isoniazid, rifampin, ethambutol, pyrazinamide, rifabutin, rifapentine, capreomycin, kanamycin, amikacin, streptomycin, fluoroquinolone antibiotics (e.g. ciprofloxacin, levofloxacin, moxifloxacin, ofloxcin, gatifloxacin), prothionamide, para-aminosalicylic acid, ethionamide, terizadone, clofazimine, clarithromycin, linezolid, amoxicillin-clavulanate, thiacetazone, bedaquiline, delamanid, carbapenmem antibiotics (e.g. imipenem, meropenem and doripenem). capreomycin, viomycin, enviomycin, rifabutin, macrolides, thioridazine, arginine, vitamin D, and bedaquiline.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Stability Tests of Commercially Available D-Cycloserine

1. Stress Testing of D-cycloserine Stability test was held with 500 mg of commercially available D-cycloserine from Macleods Pharma, opened and stored under high humidity (>90% RH or 75% RH) at room temperature, a high temperature (40° C. or 60° C.) or a light condition for 10 days. The results indicate that the D-cycloserine is sensitive to high humidity, relatively sensitive to light, relatively stable at 40° C. and 60° C., as shown in Table 1. In the following experiments, the total impurity was set up to confirm the stability of D-cycloserine.

TABLE 1

Stability tests of D-cycloserine
D-cycloserine (Macleods Pharma)

| Condition | Appearance | Moisture-absorption Weight Gain (%) | Total Impurity (%) |
|---|---|---|---|
| 0 day | White Powder | N/A | 0.59 |
| 60° C., 10 days | White Powder | N/A | 0.66 |
| 40° C., 10 days | White Powder | N/A | 0.70 |
| 25° C., >90% RH, 10 days | White Powder, Caking | 21.11 | 86.64 |
| 25° C., 75% RH, 10 days | White Powder, Caking | 0.25 | 1.71 |
| Light, 10 days | White Powder | N/A | 0.96 |

2. Stability of Combination of D-cycloserine, and Other Excipients Since humidity is a stability issue for the combinations of D-cycloserine, several excipients were chosen to test their influences on the stability under a stress condition (75% RH and 40° C.). The results are shown in Table 2. Comparing with lactose and microcrystalline cellulose pH-102 (MCC pH-102, also named as Avicel pH-102, a microcrystalline cellulose having a moisture content of 3-5%) (sample 1) or mannitol and microcrystalline cellulose pH-102 (sample 2), microcrystalline cellulose pH-102 alone (sample 3) has a better effect in stabilizing the combination of D-cycloserine in the composition. The findings reveal that samples 2 and 3 perform better in the stability tests.

TABLE 2

Stability tests of D-cycloserine mixed with different excipients

| Sample | 1 | 2 | 3 |
|---|---|---|---|
| D-cycloserine (mg) | 250 | 250 | 250 |
| Lactose (mg) | 80 | — | — |
| Mannitol (mg) | — | 80 | — |
| MCC pH 102 (mg) | 160 | 160 | 374 |
| Sodium Croscarmellose (mg) | 15.23 | 15.23 | 19.5 |
| Magnesium stearate (mg) | 5.77 | 5.77 | 6.5 |
| TOTAL (mg) | 511 | 511 | 650 |
| Total impurity in 30 days (%) | 2.76 | 1.40 | 0.89 |

Example 2: Preparation of Enteric Coated Tablets Comprising D-Cycloserine

There are three steps of preparing enteric coated tablets. The first step is preparing the core tablets compressed by S250 smart tablet press machine. The second step is preparing core tablets coated with an isolation layer material by P MINI LAB coating machine. The final step is preparing isolation layer tablets coated with an enteric layer material by P MINI LAB coating machine.

1. Compression

The active ingredients (e.g. any of the D-cycloserine compounds) were sieved by a 60-mesh screen, and the excipients were sieved by a 30-mesh screen separately. The sieved powders were mixed in a blending machine for 5 minutes to form a mixture 1. The mixture 1 was then blended with magnesium stearate as a lubricant for approximately 5 minutes, and the blend was compressed by S250 smart tablet press machine into tablets. The obtained tablets which called core tablets were weighed, and their hardness, friability, and disintegration time were tested. The dissolution release time would be tested after the enteric coating process.

2. Isolation Layer Coating 2.1. Preparing the Isolation Layer Coating Material Solution.

7493.2 g of purified water and 9894.8 g of 95% ethanol were weighed and put in a container to get a 52.47% ethanol solution. Then the isolation layer coating material (Opadry*295K680002, purchased from Shanghai Colorcon Coating Technology Ltd.) was slowly added into the 52.47% ethanol solution and stirred for 45 minutes at room temperature to get an isolation coating solution having 8% solids content. The isolation coating solution had to be continuously stirred during the coating process.

2.2 Isolation Layer Coating

P MINI LAB coating machine was preheated by setting the inlet air temperature to 40° C.-60° C. and the pan speed to 2 rpm. Then the core tablets were put into the coating machine until the exhaust temperature reached about 42° C., and then the isolation coating solution was sprayed onto the core tablets under the parameters shown in Table 3. When the coating weight gain reached the target range of 3.0±0.5%, the spraying and heating processes were stopped.

2.3 Cooling

After spraying and heating processes were stopped, the coating pan speed was adjusted to 5 rpm, and the inlet air flow was adjusted to 200-500 $m^3$/h, to cool down for 5 minutes and then the tablets coated with the isolation layer were discharged.

3. Enteric Layer Coating
3.1 Preparing the Enteric Layer Coating Material Solution.

An enteric coating material (Acryl-EZE®930640017, purchased from Shanghai Colorcon Coating Technology Ltd.) was dissolved in purified water and stirred continuously for at least 45 minutes at room temperature to obtain an enteric coating solution. Final concentration of the enteric coating solution is 20% by weight. The enteric coating solution had to be continuously stirred during the coating process with a digital overhead stirrer.

3.2 Enteric Layer Coating

P MINI LAB coating machine was preheated by setting the inlet air temperature to 40° C.-60° C. and the pan speed to 2 rpm. Then put the tablets coated with the isolation layer into the coating machine until the exhaust temperature reached about 35° C., and then the enteric coating solution was further sprayed onto the tablets coated with the isolation layer under the parameters shown in Table 3. The coating process should be closely monitored to ensure the pan temperature and the quality of the spray were satisfactory and no sticking tablets were observed. When the coating weight gain reached the target range of 12.36±0.5%, the spraying and heating processes were stopped.

3.3 Cooling

After the spraying and heating processes were stopped, the coating pan speed was adjusted to 5 rpm, and the inlet air flow was adjusted to 200-500 m$^3$/h, to cool down for 5 minutes and then the enteric coated tablets were discharged.

TABLE 3

Parameters for spraying isolation layer coating and enteric layer coating

| Parameters | Isolation layer coating | Enteric layer coating |
|---|---|---|
| Inlet Air Temperature (° C.) | 30-70 | 30-60 |
| Exhaust Temperature (° C.) | 42 | 35 |
| Pan Speed (rpm) | 6-10 | 6-10 |
| Inlet Air Flow Rate (m$^3$/h) | 400-600 | 300-600 |
| Pump flow rate (mL/min) | 40-100 | 40-100 |
| Atomization Pressure (bar) | 0.8-1.0 | 0.6-1.0 |
| Atomization Angle Pressure (bar) | 0.5-1.0 | 0.5-1.0 |

4. Hardness Test

The obtained tablets were subjected to a hardness test, and the power (N) needed for breaking the tested tablet was recorded. The harness of tablets was controlled between 120 to 160 N.

5. Friability Test

Ten tablets were put in a tablet friability apparatus and rotated at 25±1 rpm for 100 circles. The test was determined as failed if any of the tested tablets were broken. When the tablets were not broken, they would be weighted to calculate their weight loss (%). The weight loss (%) should be lower than 1%.

6. Disintegration Test

Six tablets were put into water at 37±2° C. The test was determined as failed if these tablets were not disintegrated within 30 minutes. The disintegration time (minutes) of these tablets was recorded.

7. Dissolution Test

The dissolution test was performed based on the USP method for dissolution of delayed-release dosage forms, including acid stage and buffer stage. In acid stage, six tablets were added into the first dissolution medium (0.1 N hydrochloric acid, pH 2.0) in a vessel and subjected to the dissolution test. The volume of the dissolution medium was 900 mL and the rotation speed was 100 rpm. Since the enteric coating would resist the acidic environment in stomach, the test was determined as failed if these tablets were dissolved within 120 minutes. The dissolution time (minutes) of these tablets in acid stage was recorded.

After 2 hours of operation in 0.1 N hydrochloric acid, the fluid in the vessel was withdrawn, replaced with the second dissolution medium (phosphate buffer, pH 6.8) and proceed immediately as directed under buffer stage. In buffer stage, the volume of the second dissolution medium was 900 mL and the rotation speed was of 100 rpm. The test was determined as failed if these tablets were dissolved in the 0.1N HCl acid and/or not dissolved no more than 80% of the label content (i.e. D-cycloserine) at 45 minutes. The dissolution time (minutes) of these tablets in buffer stage was recorded.

Example 3: Preparation of Core Tablets Comprising D-Cycloserine

Several formulations were used to prepare core tablets, as shown in Table 4. Microcrystalline cellulose pH-102 (MCC pH-102), microcrystalline cellulose pH-112 (MCC pH-112, also named as Avicel pH-112, a microcrystalline cellulose having a moisture content of less than 1.5%), Starch 1500 and pregelatinized starch were used as diluents in the formulations. The formulation 2 comprising MCC pH-112 and Starch 1500 and the formulation 3 comprising MCC pH-112 and pregelatinized starch showed a lower hardness and a larger friability than the formulation 1.

TABLE 4

Formulations for core tablets and their hardness and friability results

| Formulation | 1 | 2 | 3 |
|---|---|---|---|
| D-cycloserine (mg) | 525 | 525 | 525 |
| MCC pH-102 (mg) | 339 | — | 249 |
| MCC pH-112 (mg) | — | 227.5 | — |
| Pregelatinized starch (mg) | — | — | 90 |
| Starch 1500 (mg) | — | 227.5 | — |
| Croscarmellose sodium(mg) | 27 | 10 | 27 |
| Magnesium stearate (mg) | 9 | 10 | 9 |
| Total core tablets (mg) | 900 | 1000 | 900 |
| Hardness (N) | 110 | 48.3 | 40 |
| Friability (%) | 0.32% | >1% | >1% |

In addition, other formulations for core tablets were also prepared, as shown in Table 5. These core tablets were also subjected to the second part of the dissolution test (buffer stage) to determine if they could be disintegrated properly, wherein the core tablets were directly added into the second dissolution medium (phosphate buffer, pH 6.8) for the dissolution test.

Hydroxypropyl cellulose (HPC) and Povidone K30 are binder agents which can improve the defect of a lower hardness and a larger friability. In formulations 4-6, HPC showed a better ability of increasing the hardness, and HPC was chosen to increase hardness. In formulations 7-10, the formulations 7 and 10 showed a shorter and satisfactory dissolution time, but the core tablet formulations 8-9 containing a high amount of HPC showed a much longer dissolution time. Therefore, the core tablet formulations 8-9 were determined as failed in the dissolution test.

TABLE 5

Formulations for core tablets and results of hardness, friability and dissolution test

| Formulation | 4 | 5 | 6 | 7 | 8 | 9 | 10 |
|---|---|---|---|---|---|---|---|
| D-cycloserine (mg) | 525 | 525 | 525 | 525 | 525 | 525 | 498 |
| MCC pH-102 (mg) | — | — | — | 219 | 405 | 375 | 246 |
| MCC pH-112 (mg) | 227.5 | 227.5 | 227.5 | — | — | — | — |
| Starch 1500 (mg) | 227.5 | 227.5 | 227.5 | — | — | — | — |
| Povidone K30 (mg) | — | 30 | — | — | — | — | — |
| HPC (mg) | — | — | 30 | 24 | 50 | 80 | 24 |
| Croscarmellose sodium (mg) | 10 | 10 | 10 | 24 | 10 | 10 | 24 |
| Magnesium stearate (mg) | 10 | 10 | 10 | 8 | 10 | 10 | 8 |
| Total core tablets (mg) | 1000 | 1030 | 1030 | 800 | 1000 | 1000 | 800 |
| Hardness (N) | 48.3 | 27.2 | 50.35 | 120 | 177 | 165 | 155 |
| Friability (%) | >1 | >1 | >1 | 0.3 | 0.28 | 0.27 | 0.26 |
| Dissolution test (buffer stage only) | | | | | | | |
| NLT 80% in buffer stage (%) | N/A | N/A | N/A | 95 | <80 | <80 | 92 |

Example 4: Preparation of Enteric Tablet Formulations Comprising D-Cycloserine The enteric tablets were prepared in accordance with Example 2. The isolation layer and enteric layer protected the active pharmaceutical ingredients from the acidic environment of the stomach. Therefore, the amounts of isolation layer material and enteric layer material were investigated, as shown in Table 6.

TABLE 6

Formulations of enteric tablets and results of dissolution test

| Formulation | | 11 | 12 | 13 | 14 | 15 | 16 | 17 | 18 |
|---|---|---|---|---|---|---|---|---|---|
| D-cycloserine (mg) | | 250 | 250 | 250 | 250 | 250 | 250 | 250 | 498 |
| MCC pH 102 (mg) | | 157 | 157 | 157 | 374 | 374 | 374 | 374 | 246 |
| Mannitol (mg) | | 157 | 157 | 157 | — | — | — | — | — |
| HPC (mg) | | — | — | — | — | — | — | — | 24 |
| Croscarmellose sodium (mg) | | 30 | 30 | 30 | 19.5 | 19.5 | 19.5 | 19.5 | 24 |
| Magnesium stearate (mg) | | 6 | 6 | 6 | 6.5 | 6.5 | 6.5 | 6.5 | 8 |
| Total core tablets (mg) | | 600 | 600 | 600 | 650 | 650 | 650 | 650 | 800 |
| Isolation layer coating | (mg) | 18 | 18 | 18 | 32.5 | 32.5 | 16.25 | 16.25 | 24 |
| weight | (%) | 3 | 3 | 3 | 5 | 5 | 2.5 | 2.5 | 3 |
| Enteric layer coating | (mg) | 49.4 | 61.8 | 74.2 | 68.2 | 95.5 | 53.5 | 66.6 | 96 |
| weight | (%) | 8 | 10 | 12 | 10 | 14 | 8 | 10 | 12 |
| Dissolution test | | | | | | | | | |
| NMT 10% at 120 min in acid stage (%) | | 4 | 0 | 1 | 0 | 0 | 0 | 0 | 0 |
| NLT 80% at 45 min in buffer stage (%) | | 35 | 80 | 79 | 95 | 95 | 79 | 96 | 95 |

Formulations 11-13 showed no acid resistance even when their enteric layer coating amount was increased. The core tablet may also play a role in acid resistance. For the content of isolation layer, isolation layer coating weight in range of 2.5-5.0% in formulation 14-17 was suggested. For the content of enteric layer, the range of 10-14% was sufficient for the enteric tablets to resist the acidic environment of the stomach, as shown in formulation 14, 15 and 17. The enteric tablets of formulation 16 absorbed little water and the shape of the tablets changed (i.e. puffed), which might be caused by its less enteric layer coating weight. By contrast, formulations 14, 15, 17 and 18 showed better results including superior acid resistance as well as superior dissolution efficiency at pH 6.8. In summary, both isolation layer, enteric layer, and their combination are important for the successful acid-resistant formulation.

Example 5: Pharmaceutical Kinetic (PK) Studies of Enteric Capsules Comprising Nano-Crystalline D-Cycloserine and Commercial D-Cycloserine in an Animal Model 1. Preparation of the Nano-Crystalline D-Cycloserine
   Process A:
   100 mg of crude D-cycloserine powder (purchased from Stride Shasun) were dissolved in 1 mL deionized water to prepare a saturated D-cycloserine aqueous solution. 10 mL of the saturated D-cycloserine solution were slowly added into 20 mL of tert-butanol or 70% methyl ethyl ketone (MEK) in ethanol or 90% MEK in ethanol and milled by sonication at 40 Hz for 1 minute simultaneously. The solution was filtered by suction filtration using a 0.2 μm filter membrane. The filtered solution was centrifuged by 10,000 rpm for 10 minutes. The collection was vacuum-dried to obtain the nano-crystalline D-cycloserine (average yield: 40.9%). The nano-crystalline D-cycloserine prepared by Process A was used for the following experiments and tests.
   Process B:
   The saturated aqueous solution of D-cycloserine was dried by a spray dryer and the spray dried D-cycloserine powder was ground by a planetary ball mill. The diameter of ground D-cycloserine powder was less than 0.2 μm.

Process C:

The saturated aqueous solution of D-cycloserine was dried by spray dryer, and the spray dried D-cycloserine powder was prepared to a second saturated aqueous solution of D-cycloserine by the same step as shown in Process A. 10 mL of the second saturated aqueous solution of D-cycloserine was slowly added into 50 mL of 70% methyl ethyl ketone in ethanol and stirred at 150 rpm by a propeller stirrer for 10 minutes, and the D-cycloserine precipitated. The precipitated D-cycloserine was collected by vacuum filtration, and dried by vacuum dry oven at 70° C. overnight. The obtained D-cycloserine was ground by a planetary ball mill. The diameter of the ground D-cycloserine powder was less than 0.2 μm.

2. Preparation of Capsule Formulations of the Nano-Crystalline D-Cycloserine and Commercial D-Cycloserine of the Invention Preparation of Capsule Formulations:

(1) Formulation A:
  the nano-crystalline D-cycloserine in size 9 in-house enteric capsule. 5.66 g Kollicoat® enteric coating material was brushed evenly on the surface of the opened size 9 Empty Porcine Hard Gelatin Capsules (Torpac), and then air-dried until the coated capsules became hard and dry. After repeating the coating and drying steps for 5 times, the opened capsules could be closed intact were ready for use. Approximately 10 mg of the nano-crystalline D-cycloserine of the invention was filled in each capsule.

(2) Formulation B:
  the commercial D-cycloserine (diameter of 73 μm) in size 9 in-house enteric capsule. Formulation B was prepared by the method for preparing Formulation A except the nano-crystalline D-cycloserine of the invention was substituted with the commercial D-cycloserine (purchased from Strides Shasun).

(3) PK Studies in a Rat Model:

Sprague-Dawley rats at age 8 weeks old were divided into different groups with 3 rats in each group. All rats were fasted overnight with free access to water before test article administration. These rats were given with single dose of the Formulations A to B by oral administration, respectively. Blood samples were collected at different time points after the oral administration in each experiment. The volume of blood collected from each animal was greater than 300 μL and these blood samples were processed to obtain plasma (greater than 150 μL) for subsequent analysis. Plasma samples were analyzed by LC-MS/MS method to determine the amount of D-cycloserine. After obtaining blood sample, brains were collected and immediately frozen and stored at −70° C. until use.

(4) LC-MS/MS Analysis:

2 μL of each plasma sample was transferred into a well of a 96-well plate. 100 μL of 0.1 ng/μL of IS (Piracetam) in acetonitrile was added into each well to precipitate proteins. The 96-well plate was vortexed for 1 min and then centrifuged at 3000 rpm for 5 mins. The supernatant is analyzed by LC-MS/MS.

The D-cycloserine analysis for plasma samples was developed by LC-MS/MS. Chromatographic column used was Atlantis HIPIC Silica 100 A 3.0×50 mm, 3 um. The mobile phase was consisted of (A) acetonitrile/Formic acid (100/0.5 (v/v)) and (B) DI water/Formic acid (100/0.5 (v/v)) with a gradient condition as shown in Table 7. The flow rate was 0.6 mL/min. The auto sampler temperature was maintained at 25° C. and the injection volume was kept at 3 μL. The total LC run time was 5.5 mins. The ionization and detection of the analyte were performed on a triple quadrupole mass spectrometer, in the positive ion mode. Quantitation was done using the MRM mode to monitor the protonated precursor→product ion transition of m/z 103.1→75.0 for the nano-crystalline D-cycloserine of the invention and to monitor the protonated precursor→product ion transition of m/z 143.2→97.8 for piracetam as an internal standard. The PK results were shown in Table 8.

TABLE 7

Mobile phase of LC-MS/MS for plasma samples

| Time (mins) | Flow Rate (μL/min) | A (%) | B (%) |
| --- | --- | --- | --- |
| 0.00 | 600 | 95.0 | 5.0 |
| 0.50 | 600 | 95.0 | 5.0 |
| 1.00 | 600 | 50.0 | 50.0 |
| 2.50 | 600 | 50.0 | 50.0 |
| 2.60 | 600 | 95.0 | 5.0 |
| 5.50 | 600 | 95.0 | 5.0 |

TABLE 8

PK Parameters of Enteric Capsules Containing nano-crystalline D-cycloserine and commercial D-cycloserine in Rats through Oral Administration

| Formulation | Tmax (hr) | Cmax (ng/mL) | AUC last (h*ng/mL) | AUC Inf (h*ng/mL) |
| --- | --- | --- | --- | --- |
| A | 0.833# | 94068# | 141669# | 141752# |
| B | 1.167# | 74132# | 129027# | 129121# | mean value (n = 3)

When the nano-crysatlline D-cycloserine was loaded in the enteric capsules, the major differences of the PK parameters were the $C_{max}$ and AUC as shown in Table 8. The $C_{max}$ and AUC of enteric capsules comprising the nano-crystalline D-cycloserine are 26% and 10% higher respectively as compared to the corresponding values of enteric capsules comprising the commercial D-cycloserine. These data indicate that nano-crystalline D-cycloserine has a better adsorption rate in pharmaceutical kinetics; for example, a greater surface area as compared to the commercial D-cycloserine.

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The term "about" or "approximately" as used herein means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A solid dosage form, comprising:
   (i) an inner core, which comprises a cycloserine compound at a concentration of about 38.4-62% (w/w), microcrystalline cellulose (MCC) at a concentration of about 30-57.5% (w/w), croscarmellose sodium, and magnesium stearate; wherein the inner core is free of mannitol and a pH adjuster;
   (ii) an enteric layer coated on the inner core, wherein the enteric layer comprises polymethacrylate, phthalate, cellulose ester, shellac, alginate, or a mixture thereof; and
   (iii) an isolation layer between the inner core and the enteric layer, wherein the isolation layer comprises a cellulose polymer;
   wherein the solid dosage form contains about 10 mg to about 1500 mg of the cycloserine compound, and wherein in the solid dosage form, the amount of the enteric layer is 10-14% (w/w) of the amount of the inner core.

2. The solid dosage form of claim 1, wherein the cycloserine compound is in particle form having a $D_{90}$ value ranging from about 0.05 µm to about 500 µm.

3. The solid dosage form of claim 2, wherein the cycloserine compound is D-cycloserine or L-cycloserine, or a pharmaceutically acceptable salt thereof.

4. The solid dosage form of claim 1, wherein the inner core comprises about 246 mg of the microcrystalline cellulose (MCC), about 24 mg of the hydroxypropyl cellulose (HPC), about 24 mg of the croscarmellose sodium, and about 8 mg of magnesium stearate.

5. The solid dosage form of claim 1, wherein the enteric layer comprises:
  (a) polymethacrylate, which is selected from the group consisting of poly(methacrylic acid-co-ethyl acrylate) in a molar ratio of 1:1, poly(methacylic acid-co-methyl methacrylate) in a molar ratio of 1:1, poly(methacylic acid-co-methyl methacrylate) in a molar ratio of 1:2, and poly(methyl acrylate-co-methyl methacrylate-co-methacrylic acid) in a molar ratio of 7:3:1;
  (b) phthalate, which is selected from the group consisting of polyvinyl acetate phthalate, hydroxypropyl methylcellulose phthalate, diethyl phthalate, and cellulose acetate phthalate; and/or
  (c) cellulose ester, which is selected from the group consisting of cellulose acetate trimellitate, cellulose acetate succinate, and hydroxypropyl methylcellulose acetate succinate.

6. The solid dosage form of claim 1, wherein the enteric layer comprises 90.5%-98.49% of poly(methacrylic acid-co-ethyl acrylate) in a ratio of 1:1 by weight, 0.5%-2% of sodium lauryl sulfate by weight, 0.01%-2.5% of triethyl citrate by weight, 0.5%-2.5% of colloidal silicon dioxide by weight, and 0.5%-2.5% of talc by weight.

7. The solid dosage form of claim 1, wherein the cellulose polymer is hydroxypropyl methylcellulose (HPMC).

8. The solid dosage form of claim 7, wherein the HPMC has an average molecular weight of 50,000 to 125,000 Dalton.

9. The solid dosage form of claim 1, wherein the isolation layer comprises 95.5%-99.49% of hydroxypropyl methylcellulose by weight, 0.5%-2.5% of talc by weight, and 0.01%-2% of triacetin by weight.

10. The solid dosage form of claim 1, which comprises about 96 mg of the enteric layer and/or about 24 mg of the isolation layer.

11. The solid dosage form of claim 1, wherein the inner core comprises MCC pH 102, croscarmellose, hydroxypropyl cellulose (HPC), and magnesium stearate; wherein the enteric layer comprises polymethacrylate; and wherein the isolation layer comprises HPMC having a molecular weight of 50,000 to 125,000 Dalton.

12. The solid dosage form of claim 1, wherein the cycloserine compound is in nanocrystalline form.

13. The solid dosage form of claim 1, which is a pharmaceutical composition, a nutraceutical composition, a health food, or a medical food.

14. The dosage form of claim 1, which is in tablet form.

15. The solid dosage form of claim 1, wherein the inner core further comprises hydroxypropyl cellulose (HPC).

16. The solid dosage form of claim 15, wherein the HPC is at a concentration of about 3% (w/w), the croscarmellose sodium is at a concentration of about 3% (w/w), and/or the magnesium stearate is at a concentration of about 1%.

17. The solid dosage form of claim 1, wherein the cycloserine compound is at a concentration of about 62% and/or wherein the MCC is at a concentration of about 30%.

18. The solid dosage form of claim 1, wherein the enteric layer is at an amount about 12% (w/w) of the inner core; and/or wherein the isolation layer is at an amount about 3% (w/w) of the inner core.

19. A solid dosage form of cycloserine, comprising:
  (i) an inner core comprising:
    (a) a cycloserine compound at a concentration of about 62% (w/w), and
    (b) pharmaceutically acceptable excipients, which comprises microcrystalline cellulose (MCC) at a concentration of about 30% (w/w), hydroxypropyl cellulose (HPC) at a concentration of about 3% (w/w), croscarmellose sodium at a concentration of about 3% (w/w), and magnesium stearate at a concentration of about 1%;
  (ii) an enteric layer coated on the inner core, wherein the enteric layer comprises polymethacrylate, phthalate, cellulose ester, shellac, alginate, or a mixture thereof, wherein the enteric layer is at an amount of about 12% (w/w) of the inner core; and
  (iii) an isolation layer between the inner core and the enteric layer, wherein the isolation layer comprises a cellulose polymer, wherein the isolation layer is at an amount of about 3% of the inner core;
  wherein the solid dosage form contains about 10 mg to about 1500 mg of the cycloserine compound.

20. A method for alleviating a symptom associated with a neuropsychiatric disease or tuberculosis, the method comprising administering to a subject in need thereof an effective amount of the solid dosage form of claim 1.

21. The method of claim 20, wherein the neuropsychiatric disorder is selected from the group consisting of schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

22. The method of claim 20, wherein the solid dosage form is administered to the subject three times a day to one time every three months.

23. The method of claim 20, wherein the subject is on an additional treatment for the neuropsychiatric disorder or wherein the subject is on an additional treatment of tuberculosis.

24. The method of claim 20, further comprising administering to the subject an additional therapeutic agent for treating the neuropsychiatric disorder or tuberculosis.

* * * * *